US00PP37713P2

(12) United States Plant Patent
Pomper et al.

(10) Patent No.: US PP37,713 P2
(45) Date of Patent: Sep. 29, 2026

(54) PAWPAW TREE NAMED 'Hi 1-4'

(50) Latin Name: ***Asimina triloba* (L.) Dunal**
Varietal Denomination: Hi 1-4

(71) Applicant: Kentucky State University, Frankfort, KY (US)

(72) Inventors: Kirk Pomper, Frankfort, KY (US); Sheri Crabtree, Frankfort, KY (US); Jeremy Lowe, Frankfort, KY (US)

(73) Assignee: Kentucky State University, Frankfort, KY (US)

( * ) Notice: Subject to any disclaimer, the term of this patent is extended or adjusted under 35 U.S.C. 154(b) by 0 days.

(21) Appl. No.: 19/314,990

(22) Filed: Aug. 29, 2025

(51) Int. Cl.
*A01H 5/08* (2018.01)
*A01H 6/00* (2018.01)

(52) U.S. Cl.
USPC ..... Plt./156
CPC ..... *A01H 6/00* (2018.05); *A01H 5/08* (2013.01)

(58) Field of Classification Search
USPC ..... Plt./156
See application file for complete search history.

*Primary Examiner* — Susan McCormick Ewoldt
(74) *Attorney, Agent, or Firm* — Patrick M. Torre; Stites & Harbison PLLC

(57) ABSTRACT

This disclosure relates to pawpaw trees, and more specifically to a pawpaw tree with pyramidal growth form and moderate vigorous growth; a superior fruit distinguished by its all-around excellent fruit quality consisting of very large, firm, yellow-orange fleshy fruits with a low seed-to-fruit ratio and an improved flavor as determined by taste tests. The number of fruit per cluster is low, often in singles, which simplifies harvesting.

3 Drawing Sheets

GOVERNMENT INTEREST

This invention was made with partial government support under grant number 7004384 awarded by the U.S. Department of Agriculture Evans Allen Research Capacity Grant Funding. The government has certain rights in the invention.

Latin name: *Asimina triloba* (L.) Dunal.

Variety denomination: 'Hi 1-4'.

BACKGROUND

This disclosure is directed to a new and distinct variety of pawpaw tree. It was discovered by the applicant in September 2011. The parents are unknown. The original tree is a seedling from mixed seed collected from the pawpaw regional variety trial planted in 1998. The original tree was not grafted onto a rootstock. Propagated trees were grafted onto pawpaw seedling rootstock with unknown parentage.

The pawpaw is the largest native edible fruit of North America and belongs to the Annonaceae family. The new cultivar, 'Hi 1-4', represents a significant improvement over existing varieties due to its very large fruit size, reliable productivity, and superior sensory attributes, with a high grafting and budding propagation success rate. Additionally, the fruit has a percent seed that is only 6.5% of fruit weight.

BRIEF SUMMARY

'Hi 1-4' originated from a seedling grown from mixed seed planted in 1998, which included a collection of 28 cultivars and advanced selections that had come from excellent seedlings. The seedling was germinated and initially cultivated in a greenhouse in 2002, then transplanted to an orchard in Frankfort, Kentucky, in 2004. It was later identified and tested under the selection code Hi1-4. In a 2016 experiment, Hi1-4 was compared to Hi7-1 (KSU-Dunnigan™), KSU-Atwood™, KSU-Benson™, KSU-Chappell™, G6-120, G9-111, G4-25, G5-23, Hy3-120, and G9-109 for grafting and budding propagation success rate. Hi1-4 had an 84% propagation success rate for whip-and-tongue grafting, cleft grafting, and chip budding techniques, which was higher than for the selections KSU-Benson™, G6-120, G9-111, G4-25, Hy3-120, and G9-109. Therefore, asexual propagation of this cultivar by budding and grafting confirmed that its unique characteristics are stable and consistently expressed through successive generations. Studies have demonstrated that orchard-grafted Hi1-4 trees are capable of producing fruit within several years after grafting, allowing growers to rapidly transition existing orchards to this selection.

The fruit of 'Hi 1-4' is notable for its very large size, yellow-orange pulp, and a tropical like flavor that is a blend of mango, pineapple, and banana. Sensory evaluation panels (Tables 1 and 2) have rated its flavor as superior to the cultivar 'Wabash' and comparable to both 'Sunflower' and 'KSU-Benson'. The fruit has a sweet, juicy, low-acid flavor with a soft texture and moderate aroma. The skin is green, while the flesh exhibits a vibrant yellow-orange coloration. Each fruit typically contains 10 to 16 dark brown seeds. Fruit ripening occurs over a three-week harvest period, with the average optimal harvest time falling during the second week of September, approximately five days earlier than the cultivar 'KSU-Atwood'. The fruit retains eating quality measured as better flesh-to-seed ratio, larger fruit, higher yields, and improved flavor as determined by controlled taste tests (Tables 1 and 2) when stored at 36° F. for up to three weeks without the need for modified atmosphere storage.

In terms of tree characteristics, 'Hi 1-4' is a moderately vigorous tree with a pyramidal growth habit. It has shown consistent annual fruiting without the need for hand thinning and demonstrates good winter hardiness under field conditions in Frankfort, Kentucky, with little observed cold injury.

'Hi 1-4' is a novel and distinct pawpaw cultivar that offers early ripening, high fruit quality, large fruit size, and excellent flavor. It is a promising new selection for commercial growers and breeders seeking superior performance and consumer appeal in pawpaw production.

BRIEF DESCRIPTION OF THE DRAWINGS

This new variety of pawpaw tree is illustrated by the accompanying photographic drawings depicting the plant by the best possible color representation, wherein.

Figure 1:
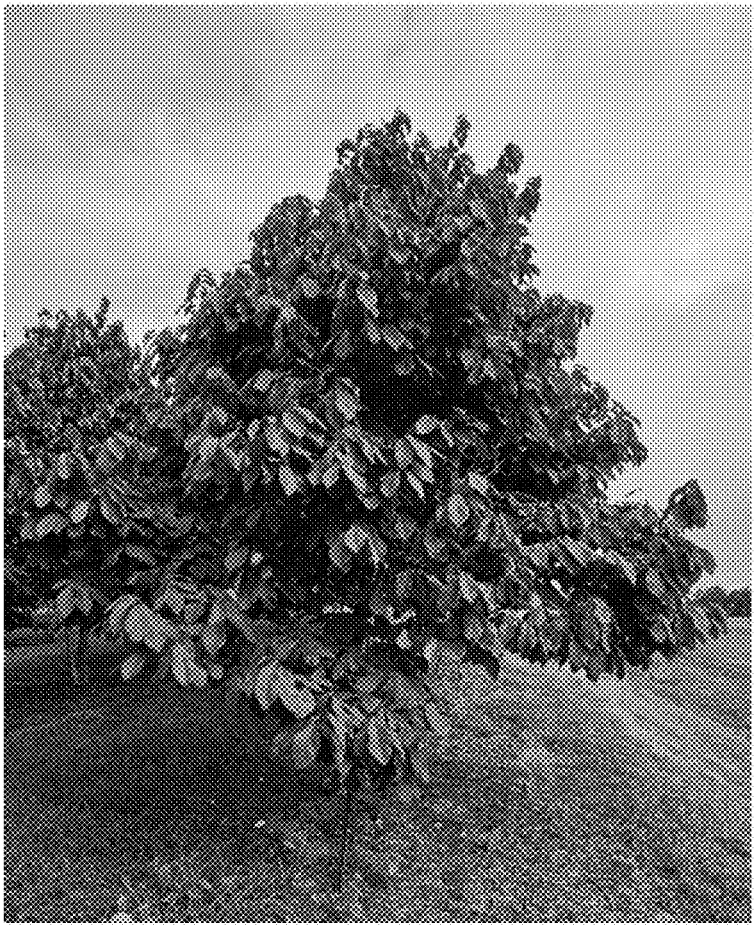
FIG. 1 is a photographic print in full color showing the form of a mature tree and the ripening fruit.
Figure 2:
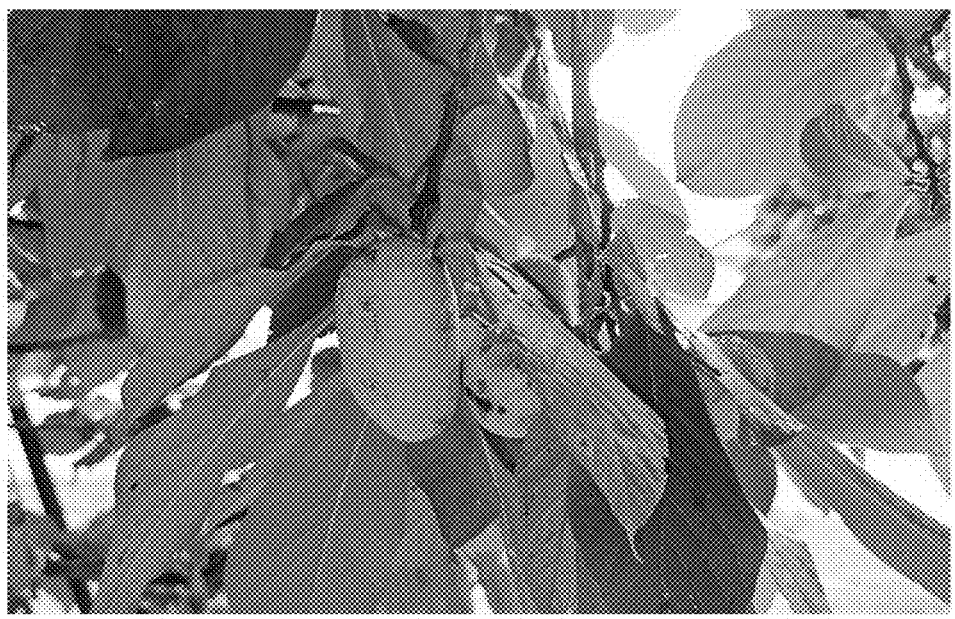
FIG. 2 is a photographic print in full color showing the maturing fruit on a section of the tree.
Figure 3:
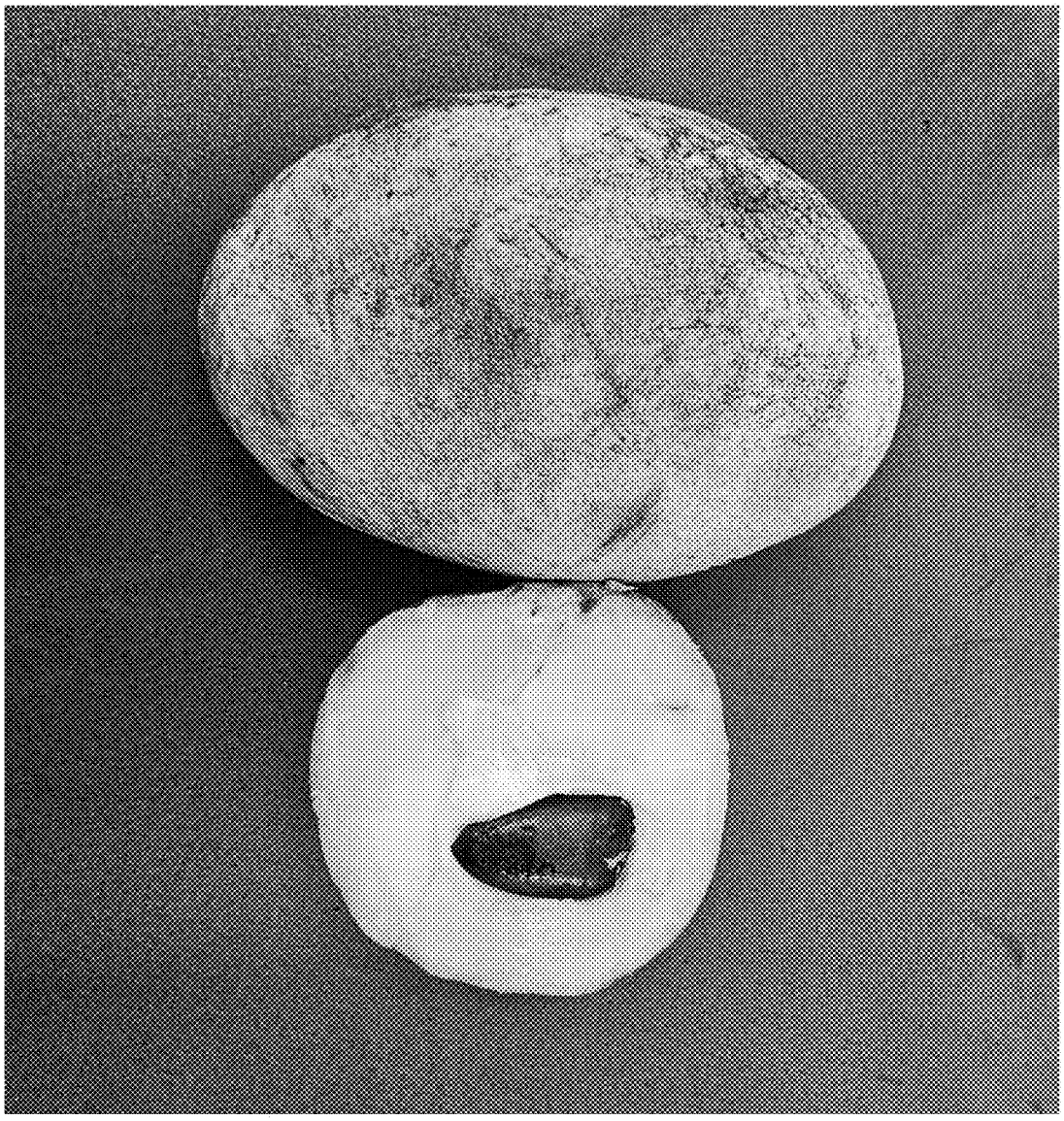
FIG. 3 is a photographic print in full color showing the ripe fruit of this cultivar.

All photographs were taken in September in Frankfort, KY.

DETAILED BOTANICAL DESCRIPTION

The following observations are believed to be characteristic of this cultivar and in combination, distinguish this pawpaw tree as a new and distinct cultivar. (Royal Horticultural Society Colour Chart, 2015, London; R.H.S. Sixth Ed.)

Tree:

*Size*.—Medium. 5-6 m on its own roots but taller on more vigorous seedling rootstock at maturity.

*Vigor*.—Medium when grafted onto seedling root stock.

*Habit*.—Pyramidal to rounded with age.

*Branching pattern*.—Spreading. Crotch angles wide. Branches widely spaced.

*Apical dominance*.—Apically dominant leader leading to a pyramidal tree form.

*Bark*.—Bark is smooth with wart-like lenticels, light grey-brown (R.H.S. 197D or 196A).

Leaves:

*Shape*.—Oblanceolate with acuminate tip and attenuate to the base, as is typical for the species. Average ratio of length to width to is 2.2.

*Size*.—Measurements are from mature leaves attached at midpoint of actively growing shoots of current season's growth. Average size is 10.0 cm wide, 22.3 cm long.

*Color*.—Upper surface varies from R.H.S. Green 139B to R.H.S. Green 141A. Lower Surface R.H.S. Green 139D. Both colors typical for the species.

*Aspect*.—Slightly drooping when grown in full sun, as is typical for the species.

*Arrangement*.—Leaves are alternate.

*Petiole*.—Color R.H.S. 141D, 142A, or 142B. Average diameter 2.9 mm at the petiole mid-point. Length had an average of 5.5 mm.

Flower:

*Size*.—Medium to Small. As the flower matures from female to male stage over several days. Size of the female stage flower — Diameter 25 to 30 mm average. Size of the male stage flower — Diameter 30-40 mm average. The flowers have a globular androecium, early stage beige R.H.S. 164D, late stage brown R.H.S. 200A or 200B, and a gynoecium light green R.H.S. 142A, usually composed of 3-7 carpels.

*Color*.—Maroon. R.H.S. Red 45A at maturity. Upper and lower surfaces of petals are the same color.

*Peduncle*.—1.5-2 cm long, green R.H.S. 141D, 1422A, or 142B, covered in a dark brown pubescence R.H.S. 165A or 200B. The flower bud is covered with a dark brown pubescence with a color R.H.S. 165A or 200B. Flower buds open April 1-May 5 in Kentucky. Vegetative buds emerge April 20-May 15 in Kentucky. The variety may produce up to 5% fruit set with self-pollination in controlled pollination tests, but cross pollination is desirable for commercial production.

Fruit:

*Dates of picking*.—Mid Season, generally from September 4 to 25 at Frankfort, Kentucky; however, dates can vary by more than a week depending on the degree of drought, high rainfall, and summer heat.

*Cluster size or fruit number*.—Average 2.5 fruit per cluster over a three-year period.

*Fruit shape*.—From broadly ellipsoidal to somewhat cylindrical with rounded ends. Shape varies greatly.

*Fruit size*.—Fruit is large, averaging 230 g, with 2.5 fruit per cluster over a three-year period.

*Skin color*.—Under-ripe fruit pale green ranging from R.H.S. Green 142D to 143D. Ripe fruit pale yellowish green, R.H.S. Green 150A to 150C. After the fruit passes its climacteric peak and falls from the tree, browning of the fruit occurs cover the entire skin surface, as is typical for the species.

*Color break*.—There is a small change in the color of the fruit after it is fully ripe, however it is not a reliable indicator for hand harvesting of early ripening fruit. Color break precedes browning of the skin when it is overripe.

*Fleshiness*.—Medium to high. Percent seed is 6.5% on average over three years.

*Flesh color*.—Creamy yellow and uniform throughout. Color ranges from R.H.S. Yellow-Orange 3A, 4A, and 5B.

*Seeds*.—Fruit usually contains 10-16 seeds that are dark brown in color.

*Aroma of cut ripe fruit*.—Pleasant. Low power.

*Flavor*.—Very Sweet, Brix 26%, mild, non-bitter, and non-astringent assessed over a three-year period. Seeds average 3 cm long, oval to bean-shaped, and have a smooth surface. Seeds can be dark brown (R.H.S. 200A, 200B, and 200C).

*Diseases and pests*.—Leaf spots can infect leaves and fruits include a complex of *Mycocentrospora asiminae, Rhopaloconidium asiminae*, and *Phyllosticta asminae*. Symptoms include light brown spots on leaves, and brown to black superficial spots on the fruit surface. Since the blackened skin is no longer expandable, continued fruit growth after infections can case fruit skin cracks exposing the flesh to bacteria and insects. This occurs occasionally with this cultivar. *Talponia plummeriana*, the Pawpaw Peduncle Borer, larvae can damage small numbers of flower peduncles killing some flowers. However, this has little or no impact on yield with the usual over of production of flowers on the tree.

*Storage ability*.—Ripening fruit will store at 36° F. for approximately 3 weeks and maintain excellent eating quality without atmosphere modification.

*Use*.—The variety has excellent quality for fresh consumption and pulp extraction for value-added product use.

The tree requires cross-pollination with any genetically distinct pawpaw for optima fruit set. Cultivars have been found to require between 650-850 chilling units to flower

TABLE 1

Consumer rankings of six pawpaw cultivars and advanced selections on fruit flavor, texture, and appearance (1 = Poor; 5 = Excellent).

| Variety | Flavor | appearance | texture |
|---|---|---|---|
| KSU-Benson ™ | 4.04 a | 3.92 | 3.91 |
| Susquehanna | 4.04 a | 3.84 | 4.00 |
| KSU-Atwood ™ | 4.00 a | 3.68 | 3.74 |
| Hi 1-4 | 3.92 a | 3.92 | 3.88 |
| Sunflower | 3.81 a | 3.92 | 3.80 |
| Wabash | 2.93 b | 3.48 | 3.26 |
| | *** | NS | NS |

TABLE 2

| Selection | Fruit Weight (g) | Percent Seed | Brix |
|---|---|---|---|
| | 2019 | | |
| KSU-Atwood | 183.2 | 6.20% | 24.3 |
| Hi 1-4 | 246.7 | 7.00% | 26.4 |
| Hi 7-1 | 182.5 | 7.60% | 26.3 |
| | 2023 | | |
| KSU-Atwood | 238.6 | 5.90% | 26.4 |
| Hi 1-4 | 214.0 | 6.85% | 24.9 |
| Hi 7-1 | 202.0 | 7.32% | 25.8 |
| | 2024 | | |
| KSU-Atwood | 160.3 | 8.00% | 23.3 |
| Hi 1-4 | 229.7 | 5.90% | 25.9 |
| Hi 7-1 | 157.7 | 9.30% | 23.0 |

We claim:

1. A new and distinct *Asimina triloba* (L.) Dunal (pawpaw) tree substantially as shown and described herein.

* * * * *